United States Patent
Rolli et al.

(10) Patent No.: US 8,468,662 B2
(45) Date of Patent: Jun. 25, 2013

(54) PRESS FOR PRODUCING A TAMPON

(75) Inventors: Kilian Rolli, Baden (CH); Peter Mueller, Zurich (CH); Axel Hammen, Lengnau (CH); Heinz Graber, Bergdietikon (CH); Viktor Madl, Schneisingen (CH)

(73) Assignee: Ruggli Projects AG, Hagendorn (CH)

( * ) Notice: Subject to any disclaimer, the term of this patent is extended or adjusted under 35 U.S.C. 154(b) by 0 days.

(21) Appl. No.: 13/381,186

(22) PCT Filed: Jun. 28, 2010

(86) PCT No.: PCT/EP2010/003841
§ 371 (c)(1),
(2), (4) Date: Feb. 10, 2012

(87) PCT Pub. No.: WO2011/000507
PCT Pub. Date: Jan. 6, 2011

(65) Prior Publication Data
US 2012/0137479 A1    Jun. 7, 2012

(30) Foreign Application Priority Data

Jun. 29, 2009    (AT) .............................. A 1010/2009

(51) Int. Cl.
*A61F 13/20* (2006.01)
*D04H 1/22* (2006.01)

(52) U.S. Cl.
USPC ........................................................ 28/118

(58) Field of Classification Search
USPC ....... 28/118, 119, 120, 116, 123; 604/385.17, 604/904, 385.18; 264/320, 324, 334; 425/392, 425/394
See application file for complete search history.

(56) References Cited

U.S. PATENT DOCUMENTS

| 5,592,725 | A | 1/1997 | Brinker |
| 6,889,409 | B2 * | 5/2005 | Friese et al. ................... 28/118 |
| 7,087,045 | B2 * | 8/2006 | Jensen ..................... 604/385.17 |
| 7,833,210 | B2 | 11/2010 | Schoelling |
| 8,029,485 | B2 * | 10/2011 | Jensen ..................... 604/385.17 |
| 2002/0151859 | A1 | 10/2002 | Schoelling |

(Continued)

FOREIGN PATENT DOCUMENTS

| DE | 101 14 786 | 10/2002 |
| DE | 102 44 874 | 4/2004 |

(Continued)

OTHER PUBLICATIONS

International Search Report of PCT/EP2010/003841, date of mailing Oct. 12, 2010.

*Primary Examiner* — Amy Vanatta
(74) *Attorney, Agent, or Firm* — Collard & Roe, P.C.

(57) ABSTRACT

The invention relates to a press (1) for producing a tampon (8) by radially pressing an absorbent material by means of compression jaws (2, 2', 3) which have respective penetrating segments (4, 5) for embossing grooves (9, 10) into the absorbent material, one compression jaw (3) the penetrating segment (5) of which is designed as a strip having flat lateral faces projecting into the compression space and one compression jaw (2, 2') the penetrating segment (4, 4') of which is designed as a rib having undulated lateral faces projecting into the compression space being alternately arranged. A projection of the strip onto a peripheral surface of the tampon (8) present in the compression space represents a straight line and a projection of the undulated rib onto the peripheral surface represents an undulated line.

8 Claims, 3 Drawing Sheets

U.S. PATENT DOCUMENTS

Figure 2:
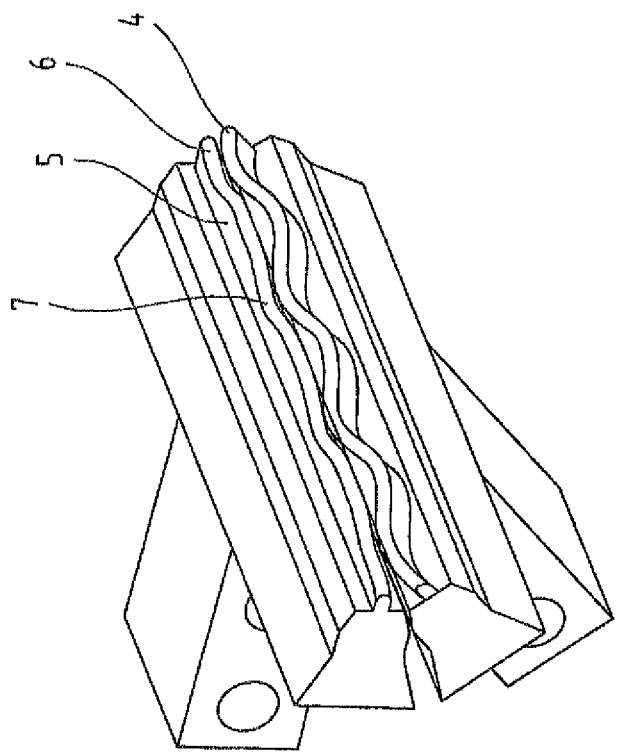

| | | |
|---|---|---|
| 2005/0113787 A1* | 5/2005 | Carlin .................. 604/385.18 |
| 2005/0113807 A1* | 5/2005 | Carlin ...................... 604/904 |
| 2008/0200892 A1* | 8/2008 | Van Ingelgem et al. ...... 604/379 |
| 2009/0082712 A1* | 3/2009 | Hasse et al. .................. 604/11 |
| 2010/0121251 A1* | 5/2010 | Van Ingelgem et al. ........ 604/11 |
| 2010/0205792 A1 | 8/2010 | Schoelling |
| 2010/0299896 A1 | 12/2010 | Schoelling |
| 2010/0299897 A1 | 12/2010 | Schoelling |
| 2012/0010587 A1* | 1/2012 | Smet ............................. 604/379 |
| 2012/0089111 A1* | 4/2012 | Magnusson et al. ..... 604/385.18 |

FOREIGN PATENT DOCUMENTS

| | | |
|---|---|---|
| DE | 10306678 A1 * | 8/2004 |
| DE | 10 2005 050514 | 4/2007 |
| EP | 0 639 363 | 5/1995 |
| WO | WO 2008/095937 | 8/2008 |

* cited by examiner

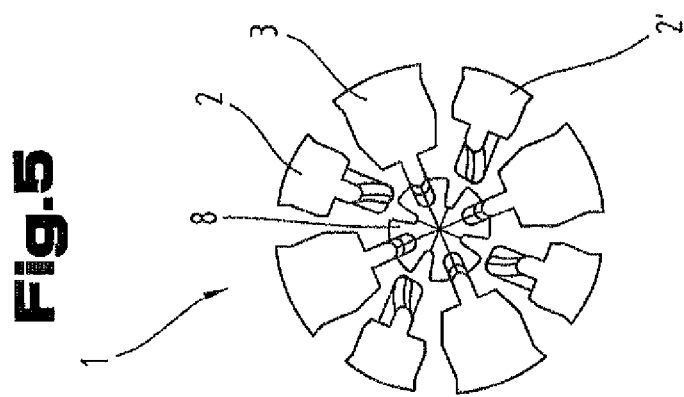
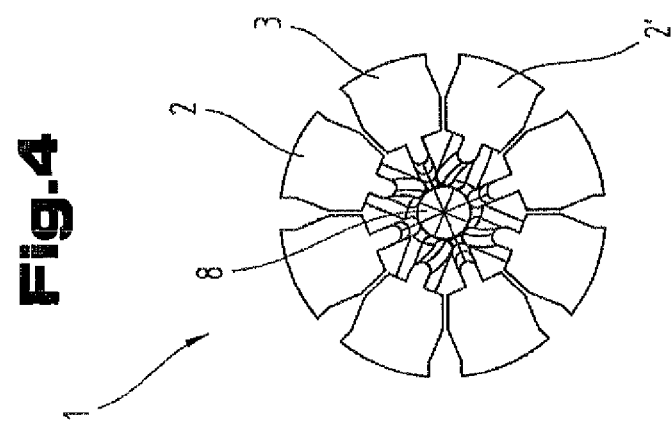
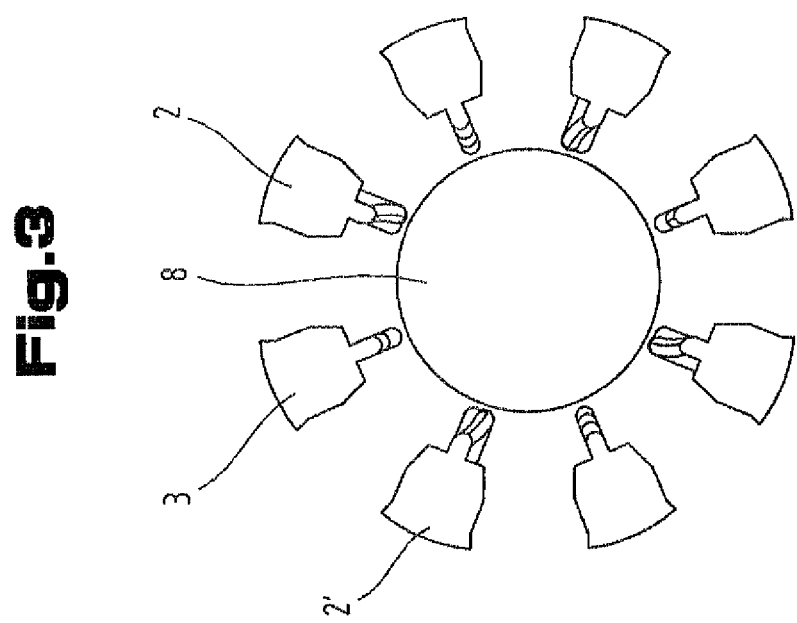

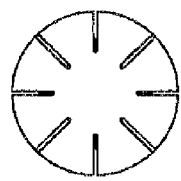
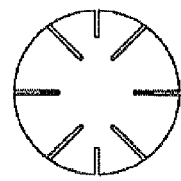
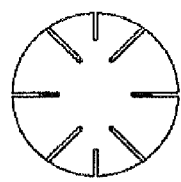
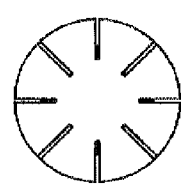
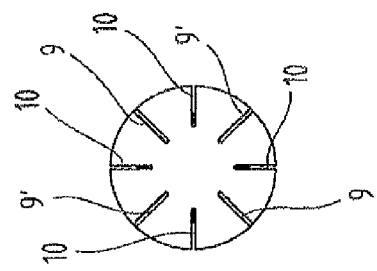
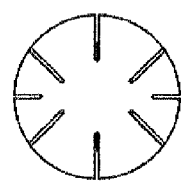
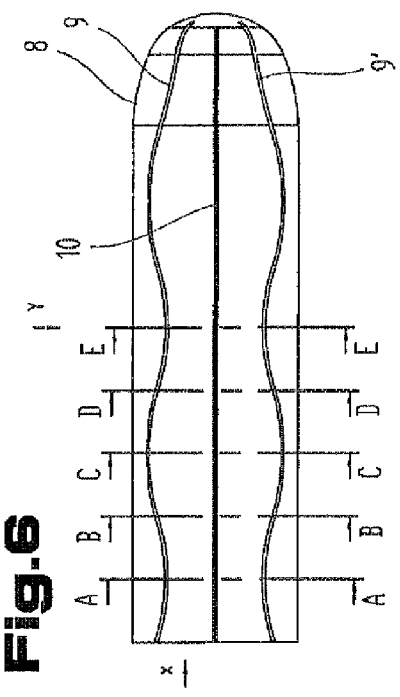
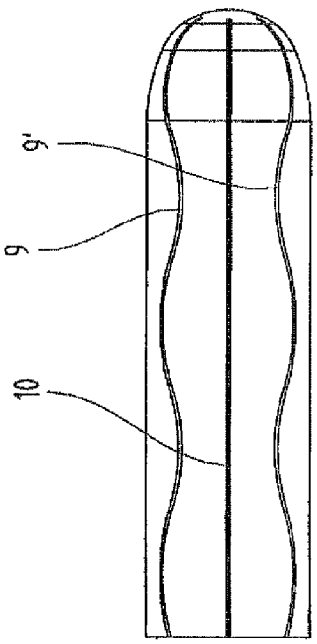

PRESS FOR PRODUCING A TAMPON

CROSS REFERENCE TO RELATED APPLICATIONS

This application is the National Stage of PCT/EP2010/003841 filed on Jun. 28, 2010, which claims priority under 35 U.S.C. §119 of Austrian Application No. A 1010/2009 filed on Jun. 29, 2009, the disclosure of which is incorporated by reference. The international application under PCT article 21(2) was not published in English.

The invention relates to a press for producing a tampon by radially pressing an absorbent material by means of compression jaws which have respective penetrating segments for embossing grooves into the absorbent material.

Furthermore, the invention relates to a method for producing a tampon by radially pressing an absorbent material by means of a press with compression jaws which have respective penetrating segments for embossing grooves into the absorbent material.

Tampons are widely known sanitary products that can be produced of strips of absorbent cotton that are rolled and subsequently compressed in a press apparatus, due to the manufacturing process typically resulting in a circular cylindrical basic shape of the tampon. From prior art many different tampons have been known for a long time, the surface properties of which are changed physically and/or chemically, to create esthetic as well as functional advantages. In this connection, press apparatuses for producing tampons providing heterogeneous surface topography—especially in the form of longitudinal grooves, having different depths if applicable, in the surface of the tampon—have been known. Such a press of the manner mentioned at the beginning has been known from the EP 0639 363 for example. The known press has compression jaws that are moveable radially to a tampon and that comprise a collar and respective penetration segments for penetrating into the absorbent material. In this case, the penetrating segments are designed as strips having flat lateral faces projecting into the compression space and the longitudinal extension of the strips essentially extends parallel to the longitudinal axis of the tampon to be processed.

The main disadvantage of this approach is that with respect to the surface of the tampon only straightly extending grooves can be produced. Grooves creating visible undulated lines at the surface of the tampon cannot be produced using this press. Additionally, a problem being connected with the production of undulated lines is that a replacement of all straight penetrating segments by undulated penetrating segments would make the ejection of the tampon out of the press considerably difficult.

It is thus the objective of the invention to overcome the above mentioned disadvantages of the prior art and to produce tampons having undulated grooves that are visible as undulated lines at the surface of the finished tampon.

With a press of the manner mentioned at the beginning, the objective is provided according to the present invention by one compression jaw the penetrating segment of which is designed as a strip having flat lateral faces projecting into the compression space and one compression jaw the penetrating segment of which is designed as a rib having undulated lateral faces projecting into the compression space being alternately arranged. A projection of the strip onto a peripheral surface of the tampon present in the compression space represents a straight line and a projection of the undulated rib onto the peripheral surface represents an undulated line.

The invention allows the embossing of undulated grooves onto the tampon that are visible as undulated lines on the finished tampon. For a process of ejection the compression jaws with the undulated penetrating segments can be retracted from the tampon completely or partially. The compression jaws having the straight strips remaining in the tampon ensure that the tampon can be removed by sliding out of the press along these penetrating segments or that said penetrating segments lead the tampon out of the press.

According to an advantageous variant of the invention, at a leading edge, the strip can provide recesses corresponding to undulations of the ribs of directly adjacent penetrating segments. Thus a reliable closing of the press without clamps or compressions or mutual interferences of the straight and undulated penetrating segments can be assured.

According to the preferred variant of the invention, two compression jaws having undulated ribs and a compression jaw having a straight strip in between provide opposed courses of their undulations.

An embodiment of the invention especially well allowing a movement of the tampon after the pressing in longitudinal direction stands out due to the fact that two compression jaws directly following one after another and having straight strips are positioned at 90° from each other and two compression jaws directly following one after another having undulated ribs are positioned at 90° from each other, too.

According to the invention, the generatrix of the undulated ribs preferably extend essentially normal to a longitudinal axis of the press. The term generatrix of the undulated ribs used herein refers to the surface lines (that means the shortest connecting lines between the points at the lower edge of the rib and the points at the upper edge of the rib) because they "produce" the surface of the rib.

Furthermore, each of the compression jaws can be moveable in radial direction and straight to the longitudinal center axis of the press.

With a method of the manner mentioned at the beginning, the objective can also be provided according to the present invention by one compression jaw the penetrating segment of which is designed as a strip having flat lateral faces projecting into the compression space and one compression jaw the penetrating segment of which is designed as a rib having undulated lateral faces projecting into the compression space being alternately arranged. A projection of the strip onto a peripheral surface of the tampon present in the compression space represents a straight line and a projection of the undulated rib onto the peripheral surface represents an undulated line. For embossing the grooves onto the surface of the tampon the penetrating segments are pressed into the tampon and after an embossing of the grooves onto the surface of the tampon penetrating segments embodied as undulated ribs are retracted out of the absorbent material meanwhile penetrating segments embodied as straight ribs remain in the absorbent material an serve as feedings for ejecting the tampon out of the press.

Figure 1:
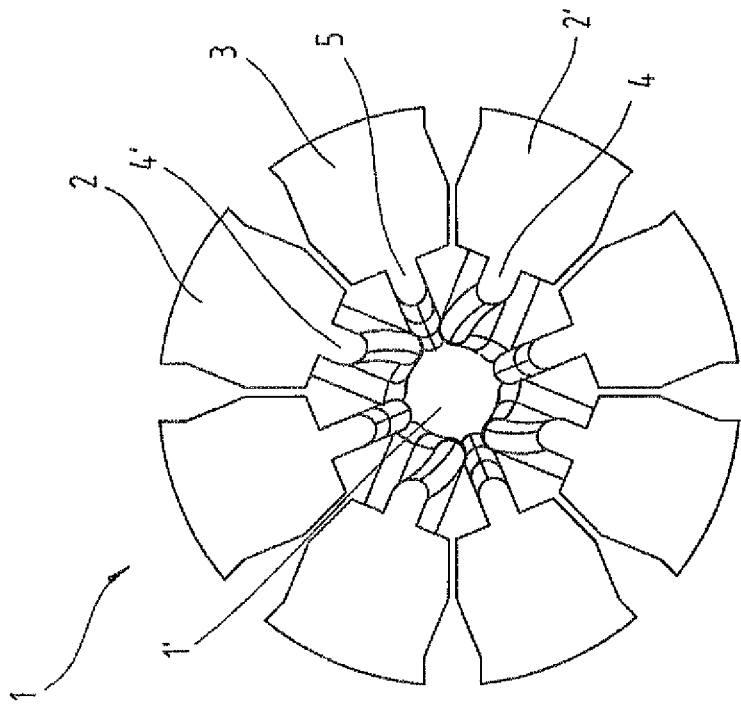

The invention providing further advantages will be explained in more detail below by means of non-restricting exemplary embodiments shown in the drawings. These show:

FIG. 1 a plan view of a press according to the invention with compression jaws approached towards one another to form a pressing position;

FIG. 2 two adjacent compression jaws of the press of FIG. 1 in detail;

FIG. 3 a plan view of the press of FIG. 1 with compression jaws moved apart from each other to form a open position and a tampon present;

FIG. 4 the press of FIG. 3 in a pressing position;

FIG. 5 the press of FIG. 3 with a tampon present after an embossing of grooves with retracted penetrating segments having undulated lateral faces;

FIG. 6 a plan view of a first side of a tampon produced with the press of FIG. 1;

FIG. 7 a plan view of the tampon of FIG. 6 from the direction y;

FIG. 8 a view of the tampon from the direction x in FIG. 6;

FIG. 9 a cross-sectional view along the line A-A of FIG. 6;

FIG. 10 a cross-sectional view along the line B-B of FIG. 6;

FIG. 11 a cross-sectional view along the line C-C of FIG. 5;

FIG. 12 a cross-sectional view along the D-D of FIG. 6 and

FIG. 13 a cross-sectional view along the line E-E of FIG. 6.

First of all, it should be pointed out that in the variously described exemplary embodiments the same parts are given the same reference numerals and the same component names, whereby the disclosures contained throughout the entire description can be applied to the same parts with the same reference numerals and the same component names. Also details relating to position used in the description, such as e. g. top, bottom, side etc. relate to the currently described and represented figure and in case of a change in position should be adjusted to the new position. Furthermore, also individual features or combinations of features from the various exemplary embodiments shown and described can represent independent or inventive solutions or solutions according to the invention.

According to FIG. 1, a press 1 according to the present invention has compression jaws 2, 3 that are arranged in star shape with respect to the press axis 1'. Compression jaws 2, 2', 3 following one after another are thus positioned from each other at an angle that can be pre-determined. In this case, the compression jaws 2, 2', 3 can be arranged with the same radial distance to the press axis 1'. Furthermore, the compression jaws 2, 2', 3 can be moved radially between an open and a closed position respective the press axis 1'. In this case it can be provided that the compression jaws 2, 2', 3 can also be moved individually or radially in groups.

The pressing of a tampon is performed by a movement of the compression jaws 2, 2', 3 towards the press axis 1' with the longitudinal axis of the tampon and the press axis 1' usually coinciding, but at least running parallel to each other. The longitudinal axis refers to the longest linear extension of the tampon. As shown in FIG. 1, the press can provide eight compression jaws 2, 2', 3. The number of compression jaws 2, 2' 3 is nevertheless not limited to the number shown and can vary dependent on the weight and the constitution of the tampon. Furthermore, the compression jaws 2, 2', 3 can be heatable.

The compression jaws 2, 2', 3 have respective penetrating segments 4, 4' and 5 for pressing the absorbent material in the form of grooves. Furthermore, the compression jaws 2, 3 can provide collars, from which the penetrating segments 4, 4' and 5 expose. Nevertheless, the penetrating segments 4, 4' and 5 can also expose directly from the compression jaws 2, 3.

As it can be seen in FIG. 2, according to the present invention there are provided two kinds of penetrating segments 4, 4' and 5 or two kinds of compression jaws 2, 2', 3. The first kind of penetrating segments 5 is designed as one strip each having flat lateral faces and the second kind of penetrating segments 4 is designed as ribs having undulated lateral faces. In this case, the producing of the undulated ribs can essentially extend normal to the press axis 1' of the press 1. Furthermore, the longitudinal extension of the penetrating segments 4, 4' and 5 extend substantially parallel to the longitudinal axis of the tampon 8.

In a mounted state of the compression jaws 2, 2', 3, the penetrating segments 4 and 5 project into the compression space. In this case, a projection of the strip onto a peripheral surface of the tampon 8 present in the compression space represents a straight line and a projection of the undulated rib onto the peripheral rib represents an undulated line.

According to the invention, a compression jaw 2, 2', which has a penetrating segment 4, 4' which is designed as a rib having undulated lateral faces and a compression jaw 3 which has a penetrating segment 5 which is designed as a strip having flat lateral faces, are alternately arranged. With regard to a straight penetrating segment 5 arranged between them, the undulated penetrating segments 4, 4' can each be arranged in a mirror-symmetry. At a leading edge 6, the strip can provide recesses 7 corresponding to undulations of the ribs of directly adjacent penetrating segments 4, 4'. These recesses 7 are positioned at the narrowest places between the adjacent undulated penetrating segments 4, 4' and the straight penetrating segments 5. The just mentioned narrowest places that means, places where the distance between the two undulated penetrating segments 4, 4' being arranged laterally to the straight penetrating segment 5 is getting minimal, can be considered as common nodal point or nodal planes of the two undulated penetrating segments 4, 4'.

Due to the recesses 7, also the leading edge 6 of the straight penetrating segments provides a shape that corresponds to the adjacent, undulated ribs. It is thus avoided that the two undulated ribs and the straight strip interfere with or block each other during the process of pressing.

As FIGS. 1, 3, 4 and 5 furthermore show, two compression jaws 3 directly following one after another and having straight strips can be positioned at 90° from each other and two compression jaws 2, 2' directly following one after another and having undulated ribs can be positioned at 90° from each other, too. Nevertheless, the invention is not limited to the angle mentioned, the compression jaws 2, 2', 3 can be arranged from each at any angle around the compression space. However, the embodiment shown is characterized by a particular good practicability.

According to FIG. 3, for shaping the grooves, a tampon 8 is inserted into the compression space positioned between the compression jaws 2 and 3. In the following, the compression jaws 2, 2' and 3 are radially moved to the direction of the tampon and this is, as shown in FIG. 4, pressed and compressed section by section, In this procedure the penetrating segments 4, 4' and 5 emboss grooves onto the material of the tampon 8. Due to the undulated penetrating segments 4, 4' and the straight penetrating segments 5, the compressed density of the tampon 8 changes.

FIG. 5 shows a press apparatus with a tampon 8 already being provided with embossed grooves fixed therein. The compression jaws 2, 2' with undulated penetrating segments 4, 4' are retracted and the straight penetrating segments 5 serve as a feeding for the tampon 8 in a direction of ejection extending parallel to its longitudinal axis or parallel to the pressing axis 1'. The ejected tampon 8 is downstream subject to another radial pressing of its complete circumference.

According to FIGS. 6 and 7, a tampon can be provided with grooves 9, 9' in the form of undulations, combined with straight grooves 10 using the press according to the present invention. The adjacent, undulated grooves 9, 9' of the tampon 8 can have opposed courses, as it can be seen in the drawings.

FIG. 8 shows a view from direction x of FIG. 6. The FIGS. 9 to 13 show cross-sectional views of a tampon 8 that was produces according to the present invention. The term cross-sectional view used herein refers to a disc that is taken perpendicular to the longitudinal axis of the tampon 8. As it can be taken from the varying depth of the resulting straight grooves, the penetration depth of the straight penetration segments 5 varies due to the recesses at their end wall.

At this point it should be noted that the invention can in principle be realized with a combination of straight penetrating segments 5 and any other shape of penetrating segments that emboss groove shapes differing from straight grooves onto the surface of the tampon 8.

The above described exemplary embodiments refer to possible variants of embodiment of an apparatus according to the inventions or a method according to the invention and are not intended to limit the scope of the invention to these illustrated variants of embodiments provided herein but that there are also various combinations among the variants of the embodiments themselves and variations regarding the present invention should be executed by a person skilled in the art. All and every imaginable variants of the embodiment, arising from combining single details of the variant of embodiment illustrated and described are subject to scope of protection.

The invention claimed is:

1. Press (1) for producing a tampon (8) by radially pressing an absorbent material by means of compression jaws (2, 2', 3) which have respective penetrating segments (4, 5) for embossing grooves (9, 10) into the absorbent material, wherein one compression jaw (3) the penetrating segment (5) of which is designed as a strip having flat lateral faces projecting into the compression space and one compression jaw (2, 2') the penetrating segment (4, 4') of which is designed as a rib having undulated lateral faces projecting into the compression space being alternately arranged and a projection of the strip onto a peripheral surface of the tampon (8) present in the compression space represents a straight line and a projection of the undulated rib onto the peripheral surface represents an undulated line.

2. Press according to claim 1, wherein a strip at the leading edge (6) features recesses (7) corresponding to undulations of the ribs of directly adjacent penetrating segments (4, 4').

3. Press according to claim 2, wherein two compression jaws (2, 2') with undulated ribs, having a compression jaw (3) with a straight strip arranged between them, provide an opposed course of their undulations.

4. Press according to claim 1, wherein compression jaws (2, 2', 3) directly following after each other are each positioned from each other at an angle that is pre-determinable.

5. Press according to claim 4, wherein two compression jaws (3) directly following one after another and having straight strips are positioned at 90° from each other and two compression jaws (2, 2') directly following one after another having undulated ribs are positioned at 90° from each other, too.

6. Press according to claim 1, wherein the generatrix of the undulated ribs essentially extend normal to a longitudinal axis (1') of the press (1).

7. Press according to claim 1, wherein the compression jaws (2, 2', 3) are moveable in radial direction and straight to the longitudinal center axis of the press each.

8. Method for producing a tampon (8) by radially pressing an absorbent material by means of a press (1) with compression jaws (2, 2', 3) with the compression jaws (2, 2', 3) having respective penetrating segments (4, 5) for embossing grooves (9, 9', 10) into the absorbent material, wherein one compression jaw (3) the penetrating segment (5) of which is designed as a strip having flat lateral faces projecting into the compression space and one compression jaw (2, 2') the penetrating segment (4, 4') of which is designed as a rib having undulated lateral faces projecting into the compression space being alternately arranged whereby a projection of the strip onto a peripheral surface of the tampon (8) present in the compression space represents a straight line and a projection of the undulated rib onto the peripheral surface represents an undulated line and for embossing grooves (9, 10) the penetrating segments (4, 5) are pressed onto the surface of the tampon (8) and after an embossing the grooves (9, 10) onto the surface of the tampon (8) penetrating segments (4, 4') embodied as undulated ribs are retracted out of the absorbent material of the tampon (8), meanwhile penetrating segments (5) embodied as strips with flat lateral faces remain in the absorbent material as feedings for ejecting the tampon (8), out of the press.

* * * * *

UNITED STATES PATENT AND TRADEMARK OFFICE
CERTIFICATE OF CORRECTION

PATENT NO. : 8,468,662 B2
APPLICATION NO. : 13/381186
DATED : June 25, 2013
INVENTOR(S) : Rolli et al.

Page 1 of 1

It is certified that error appears in the above-identified patent and that said Letters Patent is hereby corrected as shown below:

In the Claims:

In Column 6, line 34 (line 18 of Claim 8) after "tampon (8)" please insert: --,--.

In Column 6, line 38 (line 22 of Claim 8) after "tampon (8)" please delete ",".

Signed and Sealed this
Twenty-seventh Day of August, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,468,662 B2  Page 1 of 1
APPLICATION NO. : 13/381186
DATED : June 25, 2013
INVENTOR(S) : Rolli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 25 days.

Signed and Sealed this
Eighth Day of September, 2015

Michelle K. Lee
*Director of the United States Patent and Trademark Office*